United States Patent [19]

Chang et al.

[11] Patent Number: 4,873,102

[45] Date of Patent: Oct. 10, 1989

[54] MAGNETIC PARTICLES

[76] Inventors: Manchium Chang, 4589 Via Marisol, #265, Los Angeles, Calif. 90042; Michael S. Colvin, 25001 Pacific Coast Hwy., Malibu, Calif. 90265

[21] Appl. No.: 167,723

[22] Filed: Mar. 14, 1988

[51] Int. Cl.⁴ ................................................ B05D 5/12
[52] U.S. Cl. ...................................... 427/130; 264/13; 427/129; 427/214; 427/222; 427/343
[58] Field of Search ............... 427/129, 130, 128, 343, 427/222, 214; 264/13

[56] References Cited

U.S. PATENT DOCUMENTS

| | | | |
|---|---|---|---|
| 2,582,590 | 1/1952 | Heeren et al. | 427/130 |
| 2,721,357 | 10/1955 | Hochberg | 427/222 |
| 4,123,396 | 10/1978 | Rembaum | 427/222 |
| 4,438,179 | 3/1984 | Solc | 427/222 |
| 4,624,928 | 11/1986 | Margel | 427/222 |

*Primary Examiner*—Janyce Bell
*Attorney, Agent, or Firm*—Marvin E. Jacobs

[57] ABSTRACT

Magnetic polymer particles are formed by swelling porous, polymer particles and impregnating the particles with an aqueous solution of precursor magnetic metal salt such as an equimolar mixture of ferrous chloride and ferric chloride. On addition of a basic reagent such as dilute sodium hydroxide, the metal salts are converted to crystals of magnetite which are uniformly contained througout the pores of the polymer particle. The magnetite content can be increased and neutral buoyancy achieved by repetition of the impregnaton and neutralization steps to adjust the magnetite content to a desired level.

13 Claims, No Drawings

MAGNETIC PARTICLES

ORIGIN OF THE INVENTION

The invention described herein was made in the performance of work under a NASA contract and is subject to the provisions of Public Law 96-517 (35 USC 202) in which the Contractor has elected to retain title.

TECHNICAL FIELD

The present invention relates to the synthesis of magnetic polymeric particles and, more particularly, this invention relates to the preparation of small, uniform, magnetic and functional polymeric microspheres.

DESCRIPTION OF THE PRIOR ART

Magnetic particles find uses in many fields such as paints, inks, magnetic recording media in tape or disc form and oil spill clean up. Magnetic particles also find use in biology as substrates or carriers for enzymes or proteins and in cell biology as substrates derivatized with ligands capable of labelling specific cells. The labelled cells can then be separated from mixtures with unlabelled cells or from mixtures with other proteinaceous material. Magnetic microspheres can also be utilized to deliver a pharmaceutical to a specified location or organ in an animal.

Magnetic oxides and electron dense metals such as iron can also be useful in cell identification by electron microscopy. Rembaum, et al. (*Science*, 208:364, 368, [1980]) disclose identification of malignant cells in mixture with normal cells by this technique. U.S. Pat. No. 4,169,804 discloses use of magnetic-ligand particles for measurement of hormones and vitamins. Antibody-labelled magnetic microspheres have also been utilized to specifically bind to malignant cells in the treatment of leukemia (Poynton, et al., *The Lancet*, March 5, 1983, p. 524). Molday, et al., (*Nature*, 268:437–438 [1974]), U.S. Pat. Nos. 4, 157,323, 4, 177,253 and 4, 267,235 also disclose use of magnetic microspheres in the labelling and separation of specific animal cells.

Magnetic polymers have also been formed by dispersing the magnetic powders in preformed polymers. This technique is limited to soluble or meltable polymers. This process requires separation of dispersible magnetic particles. Post-polymerization apparatus and processing adds additional energy and equipment costs to the product. Magnetic polymeric materials are generally produced by suspending magnetic particles in the liquid phase of the polymerizable formulation and polymerizing the monomers in the presence of the particles to form polymeric particles. Polymerization can be by addition or condensation and can be conducted in bulk, emulsion or solution. Many of the magnetic particles are not incorporated into the resulting polymer and the size of the polymer particles must necessarily be larger than the magnetic particles. It is difficult to maintain a uniform suspension of the magnetic particles. The polymer particles do not contain a uniform amount of magnetic particles. The excess magnetic particles must be recovered from the polymerization formulation in post-polymerization processing steps.

U.S. Pat. No. 4, 339,337 discloses the preparation of magnetic beads by dispersing a magnetic filler in a solution of polymer dissolved in a polymerizable vinyl aromatic compound and polymerizing the compound. In U.S. Pat. No. 4,358,388, the magnetic filler is dispersed in an organic phase containing dissolved initiator and vinyl aromatic monomer. The organic phase is emulsified and polymerized to form a latex.

Magnetic polyglutaraldehyde microspheres are prepared by polymerization of glutaraldehyde in presence of magnetic particles (U.S. Pat. Nos. 4, 267,234 and 4,267,235) and magnetic polyacrolein microspheres are also prepared by in-situ polymerization of acrolein in presence of magnetic particles (U.S. Pat. No. 4,438,239).

U.S. Pat. No. 4,234,496 discloses the formation of magnetic polyvinyl pyridine beads by complexing the amine group with metal salts and reducing the complex to form finely divided free metal or metal oxides. This technique is limited to complexing with certain acids and the glass transition temperature of polyvinyl pyridine is low.

Porous polystyrene particles containing magnetic iron oxide have been prepared by impregnating porous nitrated polystyrene particles with iron salt such as ferrous chloride, ferric chloride or their mixtures. Magnetic polymeric particles are formed by nitrating a polymeric substrate and then reacting the polymer with iron in presence of mineral acid as disclosed in Ser. No. 86,469 filed Oct. 11, 1985. Both these methods require pre-nitration of the polymer.

In summary, these methods do not provide polymer particles with uniform amounts of magnetic particles. It is difficult to reliably control the amount of magnetic strength of the particles nor to change the magnetic properties after polymerization. There also is no way to control buoyancy of the particles.

Statement of the Invention

An improved method of forming magnetic particles is provided by the present invention. The particles are provided with uniform magnetic properties which can be varied by repeating the method to add additional magnetic metal oxide to the polymer particles. Buoyancy of the particles can also be controlled by the amount of magnetic metal oxide added initially to the particles or during the repetition step. The particles can be rendered neutral buoyant by this method. If the polymer particles have uniform size and shape such as those prepared from uniform droplets in the zero gravity of space, the resulting magnetic particles exhibit monodispersity.

The method of the invention is very versatile, providing preparation and control of magnetic and density characteristics in a straightforward and simple manner. The magnetic metal oxides form in the interior of the polymer particles and are locked in the pores. The magnetic particles are retained in the pores and are not lost by abrasion or swelling of the particles.

The properties of the magnetic polymeric polymer can also be controlled by appropriate selection of the properties of the polymer particle. The domain size and the distribution of the magnetic oxide can be controlled by the pore volume and cross-link density of the polymer particles. This, of course, affects the magnetic characteristics of the particle. The amount of metal oxide absorbed by the porous polymer particle can also be affected by adding metal complexing or coordination sites to the polymer. Magnetic properties of the particles can also be enhanced by post-treatment steps such as oxidation to introduce super-paramagnetic properties according to known procedures.

Magnetic polymeric particles are formed according to this invention by adding a solution of magnetic metal ions to porous polymeric particles and allowing the ions to enter the pores. A basic reagent is then added to the solution to convert the metal ions to the oxide form. When the liquid medium is basified, magnetic crystals form inside the micropores. The magnetic metal oxide is found to be fine-grained, non-clustered and is evenly distributed throughout each sphere in the dispersion. The dispersion of the polymer particles in solution of ion followed by basification can be repeated to increase the amount of magnetic metal oxide added to the polymeric particles. Particles of different magnetic metal oxide content can be separated by a density gradient column. The particles can also be suspended in oxidizing agent to modify magnetic properties.

The magnetic polymeric microspheres produced in the method of the invention have many uses. The microspheres can be used in polymeric magnetic separation of cancer cells or in labelling and visualization of cellular structures. The particles can be used for column packing material for liquid chromatography as well as affinity chromatography. The uniformity of size and shape are major factors in the column efficiency obtained. The microsphere particles have high surface area and can be made porous, like sponges, a form in which they are useful as catalysts or catalyst supports. The pure hydrophilic materials have a low non-specific absorption of hydrophilic materials such as proteins. Their large, uniform size coupled with mechanical strength allows high flow rates and high pressures to be used without breaking the particles. Also, if a catalyst were carried on the surface of a magnetic particle, the catalyst particle could be magnetically recovered after the reaction was completed. Further, by adding various metals, such as platinum, the particles themselves could be rendered catalytic. The magnetic particles are electron dense and therefore could be used to visualize biological or other structures in an electron microscope without the necessity to coat the particle with gold. Instruments, filters and the like can be calibrated using the very uniform particles produced in the invention. New forms of paint or metal coatings for data storage can be fabricated using microsphere particles produced by the invention. The microspheres will also find use in diagnosis, therapy and drug targeting.

These and many other features and attendant advantages of the invention will become apparent as the invention becomes better understood by reference to the following detailed description.

DETAILED DESCRIPTION OF THE INVENTION

The magnetic metal ion can be any magnetically susceptible metal or attractable ion that forms an oxide on neutralization. The metal can be iron, cobalt, nickel or alloys thereof or other metals such as alkali or rare earth metals to form ceramic type magnetic oxide such as lithium ferrites. The preferred magnetic materials are magnetic iron oxide of the formula $Fe_3O_4$ and $Fe_2O_3$.

The metal oxide precursor is provided in the form of a metal salt that is soluble in water so that the ions can diffuse into the pores of the polymer and is readily converted to the oxide form with a basic reagent. Preferred salts are the salts of strong inorganic acids such as the halides or sulfates, preferably chlorides. Magnetite is formed utilizing a mixture of ferrous and ferric salt such as the chloride. Most efficient utilization of the iron ions occurs when the mixture is equimolar in ferrous chloride and ferric chloride. The solution of metal salt is preferably saturated in the metal salt. The impregnation of the metal ion is a diffusion process. The rate of diffusion increases with temperature. The impregnation step is usually carried out at a temperature from about 20° C. to about 50° C. The salt solution is preferably filtered to remove impurities before addition of the polymeric microspheres.

The basic reagent can be any base that converts the metal salt to a metal oxide. Preferred bases are the strong inorganic hydroxides such as the alkali metal and ammonium hydroxides such as sodium, potassium, lithium or ammonium hydroxides. The basic reagent can be utilized in a concentration from 1N to 5N, usually about 2N.

The microspheres utilized in the process of the invention are microporous to allow diffusion of the metal ions into the interior of the microsphere and to distribute the metal ions uniformly throughout the microspheres. The magnetic microspheres usually contain at least 10 percent by weight of magnetic metal oxide, usually from 3 percent to 50 percent by weight.

Preferred microspheres are swellable in aqueous medium which aids in transport of the metal ions into the interior of the microsphere. The rate of metal binding and the amount of metal uptake can be enhanced by the addition of a metal complexing agent to the polymer microsphere. The complexing agent can be added to the swelled polymer in a post-polymerization impregnation technique or the complexing agent can be added during polymerization. The complexing agent can be physically bound within the porous, cross-linked polymer or interpolymerized with the polymer. Usually the complexing agent is added to the polymer in a minimum amount of 0.5phr. Suitable complexing agents are metal chelating agents such as EDTA.

The porous particles can have any size but usually are produced in size ranging from 100 Angstroms to 1000 microns. The porous polymeric particles can be formed from widely varying polymers such as hydrocarbon addition polymers, hydrophobic hydrocarbon addition polymers, e.g., divinyl benzene cross-linked polystyrene, naturally occurring polymers such as agarose ion-exchange resins such as sulfonated or aminated cross-linked polystyrene or hydrophiolic, functionally substituted addition polymers. The latter polymers are preferred for biological use since hydrophilic polymers generally exhibit less non-specific binding to proteins or to cells and has covalent binding sites available for binding to proteins such as antibodies, to fluorescent dyes or to substrates or carriers.

Functionally substituted hydrophilic polymers are readily formed from monomer mixtures containing 25 to 95 percent of mono-unsaturated bonding monomers that are freely water soluble. These monomers are suitably selected from amino, carboxyl, aldehyde or hydroxyl substituted acrylic monomers. Exemplary monomers are acrylamide (AM), methacrylamide (MAM), acrylic acid (AA), methacrylic acid (MA), acrolein, dimethylaminomethacrylate or hydroxy-lower alkyl or amino-lower-alkylacrylates such as those of the formula:

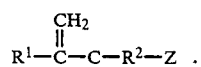

where $R^1$ is hydrogen or lower alkyl of 1-8 carbon atoms, $R^2$ is alkylene of 1-12 carbon atoms, and Z is —OH or where $R^3$—N—$R^4$ where $R^3$ or $R^4$ are individually selected from H, lower alkyl, or lower alkoxy of 1-8 carbon atoms. 2-hydroxythyl methacrylate (HEMA), 3-hydroxypropyl methacrylate and 2-aminoethyl methacrylate are readily available commercially. The porosity and hydrophilicity increase with increasing concentration of these monomers.

Inclusion of polyunsaturated compounds also provides cross-linked beads which are less likely to agglomerate. The polyunsaturated compounds are generally present in the monomer mixture in an amount from 0.1-500 percent by weight, generally 1-20 percent by weight and are suitably a compatible diene or triene compound capable of addition polymerization such as ethylene glycol dimethacrylate, trimethylol-propane-trimethacrylate (TMPTA), N,N,'-methylene-bis-acrylamide (BIS), hexahydro-1, 3, 5-triacryloyl-s-triazine or divinyl benzene (DVB).

In order to form particles having a very small size, the monomer mixture preferably contains a large percentage, suitably from 40-70 percent, of sparingly water soluble monomers having hydrophobic characteristics since this is found to result in freely suspended individual small beads. In the absence of such monomers, the particles are relatively large in diameter. Initiator and surfactant concentrations also have a pronounced effect on the particle size. Hydrophobic characteristics can also be provided with monomers such as alkyl acrylates, suitable methyl methacrylate or ethyl methacrylate or a vinyl pyridine. Suitable vinyl pyridines are 2-vinyl pyridine, 4-vinyl pyridine and 2-methyl-5-vinyl pyridine.

Fluorescence can be provided by copolymerization with addition polymerizable fluorescent comonomers such as dansyl allyl amine or functional substitute monomers such as aminofluorescein, 9-amino acridine, fluorescein isiothio-cyanate and the like. Another technique which introduces fluorescent groups into the polymer is to radiation graft acrolein to the polymer in the presence of allyl amine. An amine reactive fluorescent compound such a fluorescein isiothiocyanate can then be reacted with the polymer.

The polymerization of the hydrophilic addition polymers is conducted in the presence of a non-reactive liquid diluent miscible with the hydrophilic monomer. Preferred diluents are polar liquids such as water, lower alkyl esters of lower alkanoic acids such as ethyl acetate or lower alkanols such as ethanol. Lower is defined as materials having a carbon content of 1 to 8 carbon atoms. The diluents can be directly removed by vaporization or sublimation or indirectly removed by replacement with a liquid having a lower boiling point. Lightly cross-linked polymers may not exhibit porosity when dry due to collapse of the pores. However, when placed in a swelling agent, the polymers swell at least two times their size when dry to form pores.

Large, uniform, biocompatible particles are needed for chromatography, affinity chromatography and all separation procedures. Uniformity also provides monodispersibility. Very uniform, large microspheres (larger than 50 microns) having a coefficient of variation (C.V.) less than 3.0 are prepared by uniform freezing falling drops which are then polymerized by radiation during thawing. This procedure is disclosed more fully in co-pending application Serial No. 167,877 (Docket No. 2216), filed March 14, 1988, the disclosure of which is expressly incorporated herein by reference.

The invention will now be illustrated by the following representative examples of practice.

The procedure for the preparation of magnetic particles from preformed polymer microspheres follows: 10 ml of a saturated equimolar solution of ferric and ferrous chloride is prepared. The mixture is then filtered with a 0.5 micron filter to prevent particulate contamination of the latex. An aliquot of microspheres corresponding to approximately 1.0 gram (dry wt.) is centrifuged and the supernatant discarded. 10 ml of saturated iron salt solution is added to the pellet of microspheres and the mixture is sonicated in a bath sonicator for approximately one hour and allowed to rotate end over end for 48 hours at room temperature. The microspheres are then spun down on a centrifuge and washed quickly three times with 5 ml of distilled water, resuspending the particles to a final volume of 5 ml. 10 ml of a 10 molar sodium hyroxide is then added dropwise to the suspension with sonication causing the suspension to turn deep black due to the formation of magnetite. The magnetic microspheres (III) are then recovered by repeated washing with distilled water.

EXAMPLE 1- Preparation of Monodisperse Polystyrene Microspheres

Polystyrene microspheres of very narrow size distribution are prepared by the "successive seeded emulsion polymerization" technique. The method includes the use of a seed latex of smaller size (available from Dow Diagnostics) and growing the particles to a larger size in the presence of a monomer, an initiator and an emulsifier.

A 250 ml three neck bottle was charged with the following materials:

| | |
|---|---|
| monodisperse polystyrene seed | 50 ml |
| distilled water | 100 ml |
| cyclohexane | 15 ml |
| styrene | 20 ml |
| divinyl benzene | 4 ml |
| benzoyl peroxide | 0.050 g |
| sodium dodecylsulfonate | 0.150 g |

The mixture was stirred at room temperature for 18 hours to allow monomer and cross-linking reagent to swell the seed latex particles. A stream of nitrogen gas was then purged into the mixture for five minutes and temperature of reaction mixture was raised to 75° C. After 15 hours of reaction, it resulted in a latex suspension of polystyrene particles of 1.2 m in diameter with very narrow size distribution.

About 1 g of the dried, porous resin beads were soaked in 20 ml of a saturated, equimolar mixture of $FeCl_2$ and $FeCl_3$. The excess ferrous/ferric ions were removed. On addition of the dilute NaOH aqueous solution to the beads with stirring, the beads turned black and exhibited magnetic properties.

EXAMPLE 2

About 20 g of a sulfonated cross-linked polystyrene ion-exchange resin (BIO-RAD) was added to a saturated solution equimolar in $FeCl_2$ and $FeC_3$ (total of 100 ml). The top layer of solution was poured out. 50 ml of distilled water was added to the ferric and ferrous chloride saturated resin and quickly dispersed by means of a mixer. Dilute NaOH solution was added under agitation. The resin particles turned dark brown immediately and were slightly magnetic. Those brown particles were then resoaked with saturated $FeCl_2$ and $FeCl_3$ solution overnight and the same neutralizing procedure was repeated. All particles became much darker and more magnetic. This procedure was repeated one more time and particles became easily attractable by a magnet. The particles of different magnetic contents were then separated by a density gradient column. Neutral buoyant particles can be prepared by this procedure.

EXAMPLE 3

Porous polyHEMA microspheres were prepared by radiation of frozen monomer droplets. Two series of polymerizations were conducted using gamma radiation of frozen monomer droplets. Each monomer mixture shown in Table 1 contained 5 phr of Irgracure −184, a photoinitiator. The mixture was poured into a vessel and forced through a nozzle by pressurizing the vessel with nitrogen gas. The nozzle was mounted on the tip of diaphragm of a loud speaker which in turn was connected to a frequency generator. By tuning the frequency and adjusting the monomer mixture flow rate, a steady stream of monomer droplets was formed. Each of the droplets, identical in size, was collected in liquid nitrogen. The frozen monomer droplets were then irradiated by Cobalt 60 source for 4 hours at about 0.070 MRad/hr while adding excess nitrogen to the collection vessel. The irradiated droplets were then allowed to thaw very slowly in a −20 degree Celsius freezer. This thawing process took about 20 hours and during these 20 hours, the stored free radical initiated and polymerized the droplets into uniform microspheres.

TABLE 1

| | Monomer Composition | | |
|---|---|---|---|
| | HEMA (g) | Diluent (g) | TMPTA (g) |
| A. | 35 | 0 | 15 |
| B. | 35 | ethyl acetate 10 | 15 |
| C. | 35 | ethyl acetate 20 | 15 |
| D. | 35 | ethyl acetate 50 | 15 |
| E. | 35 | water 10 | 15 |
| F. | 35 | water 20 | 15 |
| G. | 35 | water 50 | 15 |

The diluent created unreactive holes i.e., the volume occupied by diluent molecules did not incorporate in the polymer matrix. After polymerization was completed, the removal of diluent by evaporation resulted in microholes throughout the particles. The porosity of these microspheres was examined by surface area measurement and by solvent swelling. For surface area determination, all samples were lyopholized and were measured by the nitrogen adsorption. For solvent swelling test, all samples were exchanged to 100% ethanol. The weight difference between the microspheres at fully swollen stage and after vacuum dried was used as the swelling capacity which is directly related to the porosity.

All runs resulted in production of uniform microspheres, 300–500 microns in diameter, dependent on the flow rate and monomer to diluent ratio.

TABLE 2

| Sample | Wet Weight (g) | Dried Weight (g) | Swollen/Dried |
|---|---|---|---|
| A | 2.29 | 0.58 | 4 |
| B | 2.91 | 0.50 | 5.8 |
| C | 2.56 | 0.36 | 7.1 |
| D | 1.95 | 0 23 | 8.2 |
| E | 2.68 | 0.62 | 4.3 |
| F | 2.49 | 0.52 | 4.8 |
| G | 2.11 | 0.40 | 5.2 |

TABLE 2-continued

Ethyl acetate is apparently a better diluent for preparing porous microspheres. This may be due to a higher miscibility with all ingredients at the initial stage and during polymerization.

EXAMPLE 4

PolyHEMA microspheres (300 micron) prepared with ethyl acetate according to Example 3 were swelled in 20 ml of a saturated equimolar mixture of $FeCl_2$ and $FeCl_3$. Once the system reached equilibrium, the $FeCl_2$/$FeCl_3$ polymer suspension was spun down and the supernatant discarded. To the pellet was added 5 ml of distilled water and microspheres were resuspended. NaOH solution was then added and microspheres turned black immediately and were strongly attracted by a magnet. SEM analysis confirmed that fine precipitate of magnetite clusters had formed throughout the microspheres.

EXAMPLE 5

Examples 3 and 4 were repeated except that the polymerization of HEMA was conducted in the presence of EDTA. A product with a higher magnetite content was achieved.

The invention permits preparation of large, uniform, magnetic microspheres in a straightforward, reproducible manner. The magnetic strength and density of the particles are readily controlled by repetition of the metal salt impregnation and neutralization steps. The magnetic metal oxide is uniformly distributed throughout the microspheres. The domain size and the distribution of the magnetite crystals within the pores of the polymer can be controlled by the pore volume and cross-linking density of the polymer. Particles with paramagnetic properties can also be prepared by the method of the invention.

It is to be realized that only preferred embodiments of the invention have been described and that numerous substitutions, modifications and alterations are permissible without departing from the spirit and scope of the invention as defined in the following claims.

What is claimed iss:

1. A method of forming a magnetic polymeric material containing particles of magnetic metal oxide distributed throughout the material comprising the steps of:
   immersing a swellable, porous polymer in an aqueous solution of a metal salt which is a precursor of said particles of magnetic metal oxide, said metal salt being a salt of a strong acid and a metal ion selected from iron, cobalt or nickel;
   swelling the polymer in said solution while diffusing said metal containing salt solution into said pores;
   adding a strong base selected from a hydroxide of a Group I metal ion or ammonium to the solution;
   reacting the base with the metal salt within the pores to form finely-divided magnetic metal oxide particles within the pores of the polymeric material.

2. A method according to claim 1 in which the porous polymer is in the form of particles.

3. A method according to claim 2 in which the particles are uniform microspheres.

4. A method according to claim 3 in which the microspheres are monodispersible and have a CV below 5.

5. A method according to claim 4 in which the monodispersible microspheres are prepared by radiation of frozen, sprayed, uniform monomer droplets to form free radicals and thawing of the droplets to initiate and polymerize the droplets into uniform microspheres.

6. A method according to claim 5 in which the microspheres are formed from a radiation curable acrylic polymer.

7. A method according to claim 6 in which the acrylic polymer contains 25-95% of freely-water soluble monounsaturated acrylic monomers substituted with amino, carboxyl, aldehyde or hydroxyl and 0.1 to 20% of a diene or triene cross-linking reagent.

8. A method according to claim 7 in which the monomer is hydroxyethyl methacrylate and the cross-linking agent is the trimethylol propane triacrylate.

9. A method according to claim 1 in which the metal salt is a mixture of ferrous and ferric salts.

10. A method according to claim 1 in which the metal salt solution is an aqueous, saturated, equimolar solution of ferrous chloride and ferric chloride.

11. A method according to claim 10 in which the basic reagent is dilute sodium hydroxide.

12. A method according to claim 1 in which the magnetic metal oxide particles are uniformly distributed throughout the polymeric material.

13. A method according to claim 1 in which the magnetic strength of the magnetic, polymeric material is increase by reimmersing the magnetic polymeric material in a further solution of a salt of said metal followed by adding basic reagent to said further solution to form additional magnetic metal oxide within the pores of the polymeric material.

* * * * *

UNITED STATES PATENT AND TRADEMARK OFFICE
CERTIFICATE OF CORRECTION

PATENT NO. : 4,873,102
DATED : October 10, 1989
INVENTOR(S) : Manchium Chang and Michael S. Colvin It is certified that error appears in the above-identified patent and that said Letters Patent is hereby corrected as shown below:

Abstract - penultimate line, change "impregnaton" to --impregnation--.

Col 1, line 43 - cancel "the".

Col 2, line 19, after "porous" add --,--.
    line 20, after "nitrated" add --,--.
    line 20, after "with" add --an--.

Col 3, line 28, after "low" add --,--.

line 46, change "hydrophiolic" to --hydrophilic--.
    line 55, cancel "bonding".

Col 5, line 3, change "R4" to --$R^4$--.

Col 6, line 62, change "$feC_3$" to --$FeCl_3$--.

Col 7, line 30, change "radical" to --radicals--.
    line 62, change "023" to --0.23--.

Col 8, line 48, change "iss" to --is--.

Signed and Sealed this

Twenty-second Day of January, 1991

Attest:

HARRY F. MANBECK, JR.

Attesting Officer    Commissioner of Patents and Trademarks